(12) United States Patent
St. Anne

(10) Patent No.: US 8,684,008 B2
(45) Date of Patent: Apr. 1, 2014

(54) METHOD AND DEVICE FOR FEMALE URINARY INCONTINENCE

(76) Inventor: Cora St. Anne, Inglewood, CA (US)

( * ) Notice: Subject to any disclaimer, the term of this patent is extended or adjusted under 35 U.S.C. 154(b) by 124 days.

(21) Appl. No.: 12/999,114

(22) PCT Filed: May 3, 2010

(86) PCT No.: PCT/US2010/033349
§ 371 (c)(1),
(2), (4) Date: Mar. 23, 2011

(87) PCT Pub. No.: WO2010/138275
PCT Pub. Date: Dec. 2, 2010

(65) Prior Publication Data
US 2011/0162661 A1    Jul. 7, 2011

Related U.S. Application Data

(60) Provisional application No. 61/181,556, filed on May 27, 2009.

(51) Int. Cl.
*A61F 5/48* (2006.01)
*A61F 13/20* (2006.01)

(52) U.S. Cl.
USPC ..................................... 128/885; 604/385.17

(58) Field of Classification Search
USPC .......... 128/885, 842–844, 893, 887, DIG. 25; 602/48, 58; 604/349, 352, 385.17; 24/DIG. 11
See application file for complete search history.

(56) References Cited

U.S. PATENT DOCUMENTS

| | | | |
|---|---|---|---|
| 3,646,616 A | 3/1972 | Keshin | |
| 3,762,415 A | 10/1973 | Morrison | |
| 3,789,828 A | 2/1974 | Schulte | |
| 3,905,372 A | 9/1975 | Denkinger | |
| 3,911,173 A | 10/1975 | Sprague, Jr. | |
| 3,929,135 A | 12/1975 | Thompson | |
| 4,191,609 A | 3/1980 | Trokhan | |
| 4,324,246 A | 4/1982 | Mullane et al. | |
| 4,342,314 A | 8/1982 | Radel et al. | |
| 4,367,732 A * | 1/1983 | Poulsen et al. | 602/56 |
| 4,463,045 A | 7/1984 | Ahr et al. | |
| 4,573,986 A | 3/1986 | Minetola et al. | |
| 4,610,678 A | 9/1986 | Weisman et al. | |
| 4,785,996 A | 11/1988 | Ziecker et al. | |
| 4,822,347 A | 4/1989 | MacDougall | |
| 4,834,735 A | 5/1989 | Alemany et al. | |
| 4,842,666 A | 6/1989 | Werenicz | |
| 4,846,819 A | 7/1989 | Welch | |

(Continued)

OTHER PUBLICATIONS

Statutory Invention Registration (SIR) No. H1602 to Brock.

(Continued)

*Primary Examiner* — Patricia Bianco
*Assistant Examiner* — Ophelia A Hawthorne
(74) *Attorney, Agent, or Firm* — Berliner & Associates

(57) ABSTRACT

A method and device for use in stress female urinary incontinence. A small, flexible adhesive patch is applied to the clitoris of a person suffering from stress female urinary incontinence. The adhesive is of a type sufficient to stimulate the mechanoreceptors located in the clitoris whereby to inhibit discharge from the bladder. The patch is formed of a backing sheet of an impervious film material containing adhesive on one side. A release liner prevents the adhesive from drying out.

9 Claims, 2 Drawing Sheets

(56) References Cited

U.S. PATENT DOCUMENTS

| | | | |
|---|---|---|---|
| 4,850,986 A | 7/1989 | Temple | |
| 4,875,898 A | 10/1989 | Eakin | |
| 4,892,535 A | 1/1990 | Bjornberg et al. | |
| 4,917,697 A | 4/1990 | Osborn, III et al. | |
| 4,920,986 A | 5/1990 | Biswas | |
| 4,944,734 A | 7/1990 | Wallach | |
| 4,950,264 A | 8/1990 | Osborn, III | |
| 5,006,394 A | 4/1991 | Baird | |
| 5,007,894 A | 4/1991 | Enhorning | |
| 5,074,855 A | 12/1991 | Rosenbluth et al. | |
| 5,131,906 A | 7/1992 | Chen | |
| 5,263,947 A | 11/1993 | Kay | |
| 5,312,384 A | 5/1994 | Temple | |
| 5,336,206 A | 8/1994 | Shichman | |
| 5,383,867 A | 1/1995 | Klinger | |
| 5,386,836 A | 2/1995 | Biswas | |
| 5,417,226 A | 5/1995 | Juma | |
| 5,509,427 A | 4/1996 | Simon et al. | |
| 5,513,659 A | 5/1996 | Buuck et al. | |
| 5,589,978 A | 12/1996 | Fantone | |
| 5,669,395 A * | 9/1997 | Thompson | 128/846 |
| 6,131,575 A * | 10/2000 | Lenker et al. | 128/885 |
| 6,179,775 B1 | 1/2001 | Thompson | |
| 6,461,340 B1 | 10/2002 | Lenker et al. | |
| 6,593,313 B2 | 7/2003 | Place et al. | |
| 6,836,684 B1 | 12/2004 | Rijkhoff et al. | |
| 6,949,067 B1 | 9/2005 | Dann et al. | |
| 6,964,643 B2 | 11/2005 | Hovland et al. | |
| 7,565,198 B2 | 7/2009 | Bennett et al. | |
| 2013/0184778 A1 | 7/2013 | St.Anne et al. | |

OTHER PUBLICATIONS

Female Pelvic Floor Disorders—Investigation and Management (Benson, J.T., ed.). Norton Medical Books (1992); Chapter 11C3 by B.C. Eriksen, Electrical Stimulation, pp. 219-231 in 15 pages.
M.I. Resnick and A.C. Novic, "Urology Secrets" (1995) Chapter 42, pp. 133-138 in 6 pages.
Product Literature for the Impress Softpatch by UroMed Corporation (1998) in 12 pages.
Feneley, Roger C.L., "Normal Micturition and Its Control" chapter in "Incontinence and its management," Croom Helm (1986) pp. 16-23 in 4 pages.
Steg "Urinary Incontinence", p. 266 Churchill Livingstone (1992) in 1 page.
Li, P; Wilding, TJ: Kim, SJ: Calejesan, AA; Huettner. Je; Zhuo, M.:Kainate-receptor-mediated sensory synaptic transmission in mammalian spinal cord: Nature, Jan. 14, 1999, 397 (6715): 161-4. (Abstract only)in 1 page.
Kouichi Ota, Tadao Yanagidani, Kazuhiro Kishikawa, Yuji Yamamori, and J.G. Collins: Cutaneous Responsiveness of Lumbar Spinal Dorsal Horn Neurons is Reduced by General Anesthesia, An Effect Dependent in Part on GABA-A Mechanisms; J Neurophysiol. 80: 1383-1390, (1998) in 14 pages.
Walker, RJ; Brooks, HL; Holden-Dye, L: Evolution and Overview of Classical Transmitter Molecules and Their Receptors; Parasitology, 1996, 113 Suppl: S3-33, (Abstract only) in 1 page.
Baron, J.: Classical and Incomplete Androgen Insensitivity Syndromes; Ginekologia Polska, Jul. 1994, 65 (7):377-86. (Abstract only) in 1 page.
Chapters 1 and 2 in Hald et al.: The Urinary Bladder, Neurology and Dynamics; Williams & Wilkins (1982), pp. ix-21 in 22 pages.
Chapters 3 and 4, pp. 22-47 of "The Urinary Bladder—Neurology and Dynamics," Lippincott (1982) in 28 pages.
Chapter 11, "Sphincter Electromyography and Other Electrophysiological Tests" in Hald et al.: The Urinary Bladder, Neurology and Dynamics; William & Wilkins (1982), pp. 118-127 in 10 pages.
Chapter 12, "Uroflowmetry and Pressure-flow Investigations" in Hald et al.: The Urinary Bladder, Neurology and Dynamics; William & Wilkins (1982), pp. 128-140 in 13 pages.
Chapter 13, "Urethral Closure Pressure Profile," in Hald et al.: The Urinary Bladder, Neurology and Dynamics; Williams & Wilkins (1982), pp. 141-150 in 10 pages.
Chapter 16, "Urinary Incontinence," in Hald et al.: The Urinary Bladder, Neurology and Dynamics; Williams & Wilkins (1982), pp. 175-203 in 29 pages.
Chapter 22, "Pitfalls and Errors in Urodynamic Assessment," in Hald et al.: The Urinary Bladder, Neurology and Dynamics; Williams & Wilkins (1982), pp. 310-329 in 20 pages.
Park, K; Goldstein, I; Andry C; Siroky, MB; Krane, RJ; Azadzoi, KM; Vasculogenic female sexual dysfunction: the hemodynamic basis for vaginal engorgement insufficiency and clitoral erectile insufficiency; International Journal of Impotence Research, Mar. 1997, 9(1):27-37. (Abstract only) in 1 page.
Bond, SJ; Seibel, N; Kapur, S; Newman, KD: Rhabdomyosarcoma of the clitoris; Cancer, Apr. 1, 1994, 73(7):1984-6. (Abstract only) in 1 page.
Baron J: Parial androgen insensitivity syndrome: Ginekologia Polska, Jun. 1994, 65(6):319-25. (Abstract only) in 1 page.
Di Benedetto, V; Di Benedetto, A; Introduction of the anterior sagittal trans-ano-rectal approach (ASTRA) as a technical variation of the Passerini-Glazel clitoro-vaginoplasty; preliminary results; Pediatria Medica E. Chirurgica, Jul-Aug. 1997, 19(4):273-6. (Abstract only) in 1 page.
Salansky, N; Fedotchev, A; Bonder, A: Responses of the venous system to low frequency stimulation and EEG rhythms: clinical implications; Neuroscience and Biobehavioral Reviews, May 1998, 22(2):395-409. (Abstract only) in 1 page.
Dasgupta, P; Haslam, C; Goodwin, R; Fowler, CJ; The 'Queen Square bladder stimulator': a device for assisting emptying of the neurogenic bladder: British Journal of Urology. Aug. 1997 80(2):234-7. (Abstract only) in 1 page.
Pacheco, P; Camacho, MA: Garcia, LI; Hernandez, ME; Carrillo, P; Manzo, J: Electrophysiological evidence for the neomenclature of the pudendal nerve and sacral plexus in the male rat; Brain Research, Jul. 25, 1997, 763(2):202-8. (Abstract only) in 1 page.
Kihara, K; de Groat, WC: Sympathetic efferent pathways projecting to the bladder neck and proximal uretha in the rat; Journal of the Autonomic Nervous System, Feb. 17, 1997, 62(3):134-42. (Abstract only) in 1 page.
Strohbehn, K; Quint, LE; Prince, MR; Wojno. KJ; Delancey, JO; Magnetic resonance imaging anatomy of the female urethra: a direct histologic comparison; Obstetrics and Gynecology. Nov. 1996 88(5):750-6. (Abstract only) in 1 page.
El Hemaly, AK; Mousa, LA: Stress urinary incontinence, a new concept; European Journal of Obstetrics, Gynecology, and Reproductive Biology, Sep. 1996, 68(1-2):129-35. (Abstract only) in 1 page.
Fletcher, TF, Applied anatomy and physiology of the feline lower urinary tract. Veterinary Clinics of North America. Small Animal Practice, Mar. 1996, 26(2):181-96, Feb. 25, 1999 (Abstract only) in 1 page.
Meyer et al. Stimulated pressure profile at rest: a noninvasive method for assessing urethral sphincter function. Urology Oct. 1998, 52(4): 679-84 (Abstract only) in 1 page.
de Groat. Anatomy of the central neural pathways controlling the lower urinary tract. European Urology 1998, 34 Suppl 1:2-6 in 4 pages.
Olsen AL et at. Urethral sphincter needle electromyography in women: comparison of periurethral and transvaginal approaches. Neurourology and Urodynamics, 1998: 17(5) 531-5 (Abstract only) in 1 page.
Sittberg et al. Cough-induced leak-point pressure. Acta Obstet Gynecol Scand 77 (1998): 1000-1007 in 8 pages.
Prieto et al. Valsalva minimal leak point pressure: a useful approximation to type III urinary incontinence. Oct. 1998, 51(8) 7839 (Abstract only) in 1 page.
Wang et al. Tension-free vaginal tape. A minimally invasive solution to stress urinary incontinence in women. J. Reprod, Med, May 1998, 43(5): 429-34 (Abstract only) in 1 page.

(56) References Cited

OTHER PUBLICATIONS

Glavind K. Use of a vaginal sponge during aerobic exercises in patients with stress urinary incontinence. Int'l Urogynecotogy Journal and Pelvic Floor Dysfunction 1997: 8(6): 351-3 (Abstact only) in 1 page.
Frauscher et al. Intraurethral ultrasound: diagnostic evaluation of the striated urethral sphincter in incontinent females. Eur. Radiol. 8, 50-53 (1998) in 4 pages.
Wyczolkowski M. Functional evaluation of the internal urethral sphincter in transrectal USG. Przeglad Lekarski, 1998. 55(3): 128-32. (Abstract only) in 1 page.
Hajivassiliou. The development and evolution of artificial urethral sphincters. J. Med. Engineering and Technology, Jul-Aug. 1998, 22(4) 154-9 (Abstract only) in 1 page.
Khullar V et al. The urethra (IPP, MUPP, instability, LPP). European Urology, 1998, 34 Suppl 1:20-2. in 3 pages.
Franceschetti GP et al. Minimally invasive treatment of female urinary incontinence due to sphincter incompetence, Chirugia Italiana, 1998, 50(1): 17-24. (Abstract only) in 1 page.
Colleselli K et al. The female urethral sphincter: a morphological and topographical study. J Urology, Jul. 1998, 160 (1): 49-54. (Abstract only) in 1 page.
Van Duin et al., A computer model of the neural control of the lower urinary tract. Neurourology and Urodynannics, 1998. 17(3): 175-96. (Abstract only) in 1 page.
Nagamatsu et al, Evaluation of clinical indexes to predict fate of pelvic nerve dysfunction. Urol. Res. 1998. 26: 319-23 in 5 pages.
Von Heyden et al. Neurotransmitters in the human urethral sphincter in the absence of voiding dysfunction. Urol. Res. (1998) 26: 299-310 in 13 pages.
O'Connell et al. Anatomical relationship between urethra and clitoris. J. Urology 1998 Jun. 159(6) 1892-7. (Abstract only) in 1 page.
McLennan et al. Supine empty stress test as a predictor of low valsalva leak point pressure. Neurourology and Urodynamics 1998, 17(2): 121-7 (Abstract only) in 1 page.
Tan et al. Female pelvic floor: endovaginal MR imaging of normal anatomy. Radiology Mar. 1998. 206(3) 777-83 (Abstract only) in 1 page.
Larosa et al. Valsalva leak point-pressure (LPP) and maximal urethral closure pressure (MUCP) in women with stress urinary incontinence (SUI). Archivio Italiano di Urolegia, Andrologia Dec. 1997, 69(55): 287-92 (Abstract only) in 1 page.
Morrison, Chapter 4. "Sensations arising from the lower urinary tract" in Torrens et al. "The Physiology of the Lower Urinary Tract," Springer-Verlag (1987) pp. 89-131 in 43 pages.
Torrens, Chapter 9, "Urodynamics" in Torrens et al. "The Physiology of the Lower Urinary Tract," Springer-Verlag (1987) pp. 277-305 in 29 pages.
Fowler et al., Chapter 10, "Clinical Neurophysiology" in Torrens et al. "The Physiology of the Lower Urinary Tract," Springer-Verlag (1987) pp. 309-330 in 22 pages.
Hale DS et al. Histologic analysis of needle biopsy of urethral sphincter from women with normal and stress incontinence with comparison of electromyographic findings. Am. J. Obstet. And Gyn. 1999 Fed. 180: 342-8 in 7 pages.
DETROL product literature (1999) in 62 pages.
Benzl JS: Vaginal dysfunction; in Benson JT (ed): Female Pelvic Floor Disorders. Norton, 1992, Chapter 13, pp. 307-311 in 5 pages.
Warrell DW: Pelvic floor neuropathy; in Benson JT (ed): Female Pelvic Floor Disorders. Norton, 1992, Chapter 9, pp. 153-165 in 13 pages.
Hollander et al.: Pelvic floor neuropathy; in Benson JT (ed): Female Pelvic Floor Disorders. Norton, 1992, Chapter 11, pp. 185-198 in 14 pages.
USA Weekend HealthSmart "Can I gain control?—Effective new therapies make living with incontinence easier," p. 14 (2006) in 1 page.
Yilmaz et at. Clitoral Electromyography. J. Urology 167 2:1 (2002) (Abstract only) in 2 pages.
Rocha et al. "Impact of Pregnancy and Childbirth on Female Rats Urethral Nerve Fibers", J. International Urogynecology vol. 18 No. 12 (2007) (Abstract only) in 1 page.
Huang et al. Preservation of pudendal afferents in sacral rhizotomies. Neurosurgery, Aug. 1997, 41(2): 411-5 (Abstract only) in 1 page.
Uher et al, "Sacral reflexes: physiology and clinical application." Dis. Colon and Rectum, Sep. 1998, 41(9): pp. 1165-77 (Abstract only) in 1 page.
Gosling JA. "Modification of bladder structure in response to outflow obstruction and ageing," Euro. Urology, 1997, 32 Suppl 1: 9-14 (Abstract only) in 1 page.
Dahrns et al. "The impact of sacral root anatomy on selective electrical stimulation for bladder evacuation." World J. Urology, 1998, 18(5): 322-8 (Abstract only) in 1 page.
Deindl FM et al. "Dysfunctional voiding in women: which muscles are responsible?" British J. Urology, Dec. 1998, 82(6): 814-9 (Abstract only) in 1 page.
Deplanne et al. "The adrenergic, cholinergic, and NANC nerve-mediated contractions of the female rabbit bladder neck and proximal, medial and distal urethra." British J. Pharmacology. Apr. 1998. 123(8): 1517-24 (Abstract only) in 1 page.
Radziszewski P et al. "The morphological aspects of the innervation of the external urethral striated sphincter." Folia Morphotogca, 1995, 54(1): 1-7 (Abstract only) in 1 page.
Jarvie et al. "Novel hydrophilic cyclic monomers in hydrogel synthesis." Biomaterials, Nov. 1998, 19(21): 1957-61 (Abstract only) in 1 page.
Akala et al. "Novel pH-sensitive hydrogels with adjustable swelling kinetics," Biomaterials, Jun. 1998, 19(11-12) 1037-47.
INTROL Bladder Neck Support Prosthesis product literature, UroMed Corporation (1997) in 6 pages.
RELIANCE Urinary Control Insert product literature. UroMed Corporation (1997) in 8 pages.
National Association for Continence—Literature (1997) in 6 pages.
"Incontinence—Urinary Leakage—A Common and Treatable Condition" Pamphlet, Kaiser Permanente (1995) in 11 pages.
"The selling of incontinence." Consumer Reports Oct. 1997 in 3 pages.
Roan S. "Campaign Gets Info to Incontinent Women," Los Angeles Times, Apr. 6, 1997 p. E3 in 1 page.
van Buren. "No One Needs to Live with Incontinence," Los Angeles Times, Apr. 6, 1997 p. E4 in 1 page.
Urinary Incontinence in Adults, National Institutes at Health Consensus Development Conference Statement (1988) in 18 pages.
Chalker at al. Overcoming Bladder Disorders. Harper and Row (1990) pp. 3, 44, and 45 in 3 pages.
Gartley. Managing Incontinence. Jameson Books (1985) p. 15 in 1 page.
Urinary Stress Incontinence—Awareness Encourages Women to Speak Up, Seek Help (1993), Daniel Freeman Memorial Hospital, in 1 page.
Incontinence: No Longer a Reason to Stay Home. Los Angeles Times Advertising Supplement Aug. 2, 1992 in 1 page.
White R. Incontinence. Encyclopedia Brittanica 1985 Medical and Health Annual pp. 335-338 in 4 pages.
Activities of inventor Cora St. Anne described in the accompanying Information Disclosure Statement Transmittal submitted herewith on Nov. 14, 2013 in 6 pages.
B. C. Eriksen "Electrical Stimulation", p. 223.
M. I. Resnick, et al., "Urology Secrets", Chapter 42, pp. 133-138.

\* cited by examiner

METHOD AND DEVICE FOR FEMALE URINARY INCONTINENCE

CROSS-REFERENCE TO RELATED APPLICATIONS

This application claims the benefit of U.S. Provisional Patent Application No. 61/181,556 filed May 27, 2009, which is hereby incorporated by reference in its entirety.

FIELD OF THE INVENTION

The invention relates to a method and device for relieving or mitigating the problems associated with female urinary incontinence.

BACKGROUND OF THE INVENTION

Female urinary incontinence is a troublesome problem for many individuals and can be classified into four major categories. From least to severe:
- stress incontinence, in which a slight urine loss occur due to the momentary pressure caused by sneezing, coughing, laughing, or simply lifting a heavy object;
- urge incontinence, in which a strong frequent desire to void is accompanied by involuntary urination within a minute or two of the urge;
- overflow incontinence, which occurs when the bladder fills beyond capacity, creating pressure which exceeds urethral resistance—no urge to urinate is present, so the bladder just overflows; and
- continuous incontinence, which is a conscious or unconscious urination, which is usually the result of an abnormal passage caused by surgery, trauma, or neural damage.

A number of devises have been proposed to deal with female urinary incontinence, represented by, for example, U.S. Pat. Nos. 5,074,855 to Rosenbluth et al., 6,131,575 to Lenker et al., 6,461,340, to Lenker et al., 3,789,828 to Schulte, 5,509,427 to Simon et al. 4,892,535 to Björnberg et al., 6,179,775 to Thompson, 6,836,684 to Rijkhoff, and Statutory Invention Registration (SIR) No. H1602 to Brock, the disclosures of each of which are hereby incorporated herein by reference.

Rosenbluth et al. and both Lenker et al. patents disclose a resilient pad configured to seal against and occlude the urethral meatus, i.e., the urethral opening. These devices are described as shaped and sized to fit each individual user's anatomy, implying that the application of this device requires careful attention for a comfortable fit. Moreover, the devices are designed for individual custom fitting, calling for predetermined sizes to be trimmed individually for optimal fit, including the use in some cases of a mold of the relevant portions of the vulva taken prior to sizing the pad. A mirror or light is suggested to facilitate insertion, indicating that the devices are difficult to apply and suggests that the device may be designed for clinical use, attended by a physician or health care professional. Moreover, these devices do not appear to be designed for highly active women, e.g. running, jogging, high and low impact aerobics or any exercise where the movement of the lower torso is essential. The devices are rigid around the perimeter contributing to discomfort as used in its intended position. In addition, the complex construction and individual custom fitting indicates a probable high overall cost to the consumer.

Lenker et al. U.S. Pat. No. 6,131,575 discloses in addition to the rigid female incontinence device, a more flexible device but only for male incontinence, shown in their FIGS. 26 to 30, and which is retained on the glans of a patient's penis by an adhesive layer formed of a pressure-sensitive hydrophilic hydrogel.

The device described in Shulte's patent is a mechanical device surgically implanted for prolonged use and features a fluid flow valve which can be operated manually, in contrast to the present invention's simplicity, ease of use and temporary nature as needed at the discretion of the user. In structure, the Shulte device appears to be a rigid mechanical device with a valve. Simon et al.'s device is designed to be inserted directly inside of the urethra with an "expandable balloon at its proximal end," again, which is in total contrast to our present invention. Björnberg et al. and Brock describe absorbent pads of the type that can be used as incontinence pads. Brock further describes a continuous layer of adhesive for securing the pad to a wearer's skin. The pads of both Björnberg et al. and Brock are intended to cover large general areas.

Thompson describes a device to enhance clitoral stimulation during intravaginal intercourse, using a hydrophilic, non-allergenic adhesive to seat a foraminous, elongated, generally triangular shaped pad in the female vestibule to lie beneath the labia minora to support and engage the ventral aspect of the clitoris when it is engorged with blood during the arousal phase of female sexual stimulation.

Rijkhoff et al. describes a device that uses an implanted sensor and means for generating electrical pulses to stimulate nerves to inhibit contraction of the detrusor, the muscle that expels urine from the bladder. It recognizes what has been shown by investigators, that activation of afferent nerve fibres, innervating mechanoreceptors located in the clitoris, has a strong inhibitory effect on the bladder.

BRIEF SUMMARY OF THE INVENTION

The present invention provides a method and device for use in stress female urinary incontinence. Somewhat as in the electrical stimulation of mechanoreceptors located in the clitoris, the present method physically stimulates the clitoris to provide a strong inhibitory effect on the bladder, relieving stress urinary incontinence. Notwithstanding the ability to completely relieve, stress incontinence, the device is remarkably simple. Unlike prior devices, it is not an absorbent pad to catch urine, it is not a clinical device that requires help in insertion, it does not have a rigid or semi-rigid component, nor does it have projections, and is not a complicated electronic impulse generator; moreover, the device can be used in the absence of intravaginal intercourse. It is a small, flexible adhesive patch of a size that can be comfortably applied to the clitoris either directly to the clitoral shaft or to the clitoral hood. The patch is formed of a backing sheet of an impervious film material containing adhesive on one side. A release liner prevents the adhesive from drying out.

More particularly, A method is provided for treating stress female urinary incontinence, comprising applying an adhesive directly to the clitoris of a person suffering from stress female urinary incontinence. The adhesive is of a type sufficient to stimulate the mechanoreceptors located in the clitoris whereby to inhibit discharge from the bladder, preferably a hydrophilic, non-allergenic adhesive. The adhesive is provided by the application of the adhesive layer of the above-described patch to the clitoris either directly to the clitoral shaft or to the clitoral hood. In a more particularized embodiment, the method involves identifying persons in need of a device or a method for treating stress female urinary incontinence.

The present invention provides a simple, low cost solution to a vexing problem, making it affordable and available. It is designed to comfortably fit any human female who suffers from urinary incontinence and includes all the necessary elements that compliment comfort, ease of use and confidence. The device is produced with soft, pliable materials that allow the user to continue daily routines with no discomforts or embarrassing interruptions. The present invention is also designed to permit the user to apply the device with no assistance, whatsoever, from anyone.

This device can be produced in various sizes, e.g. small, medium and large, to accommodate the over the-counter market. It is well suited for highly active women, e.g. engaging in running, jogging, high or low impact aerobics or any exercise where movement of the lower torso is essential. The product is very portable and can be available in individually sealed and sterilized packages of multiple units, which can easily fit into the average sized purse or pouch. The cost, comfort, simplicity, portability and ease of use attributed to this device, surpasses all other products presently available in the consumer's over-the-counter market.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

Figure 1:
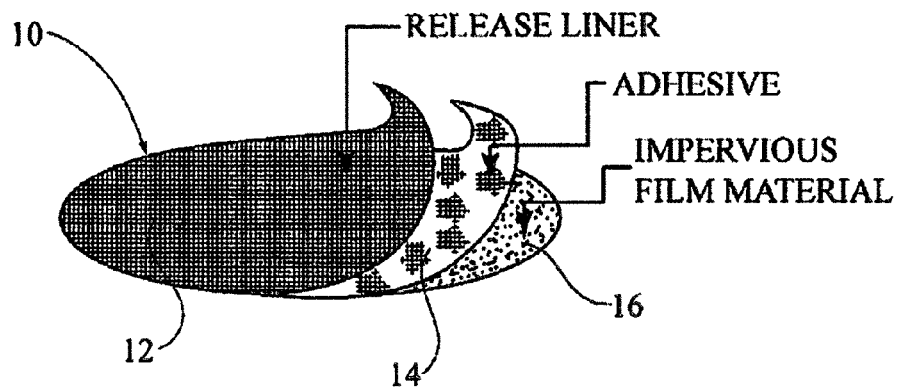
FIG. 1 is a perspective view of the device, in this embodiment having an oval shape, shown with a portion peeled up to better illustrate its construction.
Figure 2:
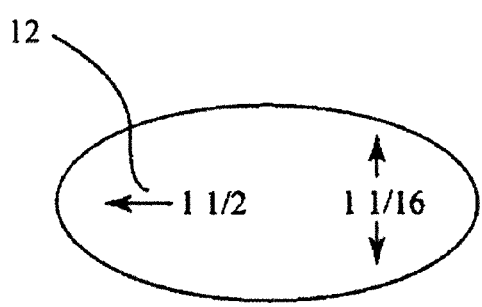
FIG. 2 is a top plan view of the device of FIG. 1.

Referring to FIGS. 1 and 2, a generally oval patch 10 of this invention is shown formed of a backing sheet 16 coated with a layer of adhesive 14 and covered with a release sheet/layer 12. The adhesive layer 14 is preferably pressure sensitive, hydrophilic and non-allergenic, as known to the art. The patch is approximately 1½ inches long and 1 1/16 inches wide.

The backing sheet 16 is preferably impervious to body fluids (e.g., urine and/or menses) and is preferably manufactures from a thin, flexible plastic film, although other flexible liquid impervious materials may also be used, all as known to the art. As used herein, the term "flexible" refers to materials which are compliant and will readily conform to the general shape and contours of clitoris region. The backing sheet 16 material may as described for the backsheet material of Brock SIR No. H1602, incorporated herein by reference, and can comprise a woven or nonwoven material, polymeric films such as thermoplastic films of polyethylene or polypropylene, or composite materials such as a film-coated nonwoven material, illustrated by a polyethylene film having a thickness of from about 0.012 mm (0.5 mil) to about 0.051 mm (2.0 mils).

The release layer/sheet 12 keeps the adhesive from drying out and can be formed of an adhesive releasing material, as known by the art, and as also illustrated in Brock SIR No. H1602. Other non-limiting examples of the adhesive releasing material/sheet includes paper, resin film, nonwoven fabric, and nonwoven fabric laminated with resin film, each having been treated with silicon. The release layer is removed before applying the patch 10.

The adhesive layer can comprise of a hydrophilic adhesive composition which may be sticky, viscous gel, or a substantially solid composition. The adhesive layer can also comprise of pressure sensitive adhesives (PSA) made from polymer such as acrylic and methacrylic ester homo- or copolymers, butyl rubber-based systems, silicones, urethanes, vinyl esters and amides, olefin copolymers, butyl rubber-based or synthetic rubbers, and the like. In another embodiment, the adhesive layer can comprise of bioadhesives (BAs), as known to the art. In contrast to PSAs that adhere mainly to dry substrates, BAs exhibit good tack when adhered to hydrated biological substrates/tissues. Non-limiting examples includes slightly cross-linked polyacrylic and polymethacrylic acids as well as blends of hydrophilic cellulose derivatives (40-95%) with polyethylene glycol. In other embodiments, the adhesive layer can comprise different combinations of PSA and BA polymeric materials of different hydrophilicity and thus different solubilities in water or in the liquids secreted by the tissue area in contact with the adhesive layer.

Regardless of the adhesive composition used, the final adhesive layer should preferably be pressure sensitive, hydrophilic and non-allergenic.

While a single patch 10 is shown in FIG. 1, in actual production and/or sale, a plurality of such patches may be formed on a single release sheet and sold as a kit whereby individual patches can be removed and applied as needed.

Figure 3:
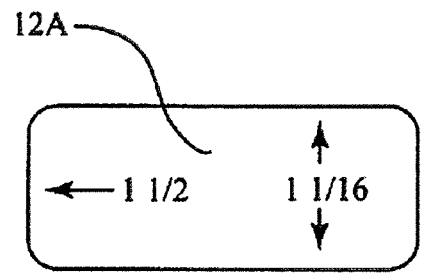
FIG. 3 is a top plan view of a device similar to the device of FIG. 1, but having a rectangular shape.

FIG. 3 shows a patch constructed in the same manner as the patch of FIG. 1, but having a generally rectangular shape 1½ inches long and 1 and 1/16 inches wide.

Figure 4:
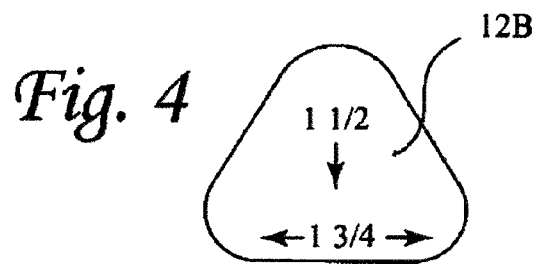
FIG. 4 is a top plan view of a device similar to the device of FIG. 1, but having a triangular shape.

FIG. 4 shows a patch constructed in the same manner as the patch of FIG. 1, but having a generally triangular shape 1 and ½ inches high and 1 and ¾ inches at its base.

Figure 5:
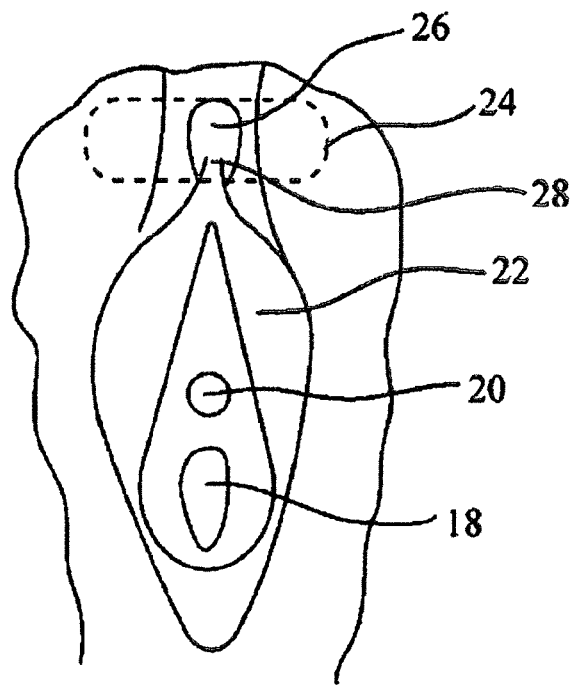
FIG. 5 is a sketch of a vagina illustrating components relevant to the invention.
Figure 6:
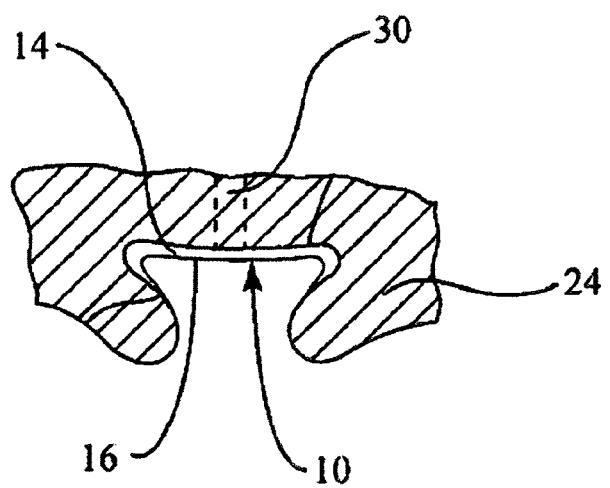
FIG. 6 is a cross-section of the clitoral region of the vagina, showing application of the patch of FIG. 1.

The patch 10 is applied with the adhesive layer to the clitoris. FIG. 5 is a sketch of a vagina illustrating relevant components of a vagina, including the vaginal opening 18, the urethral opening 20, the labia minora 22, the labia majora 24, the clitoral hood 26 and the clitoris at 28. As shown in FIG. 5, the adhesive can be applied to the clitoral hood 26 or as in FIG. 6 directly to clitoral shaft 30. Referring specifically to FIG. 6, the patch 10 is applied between opposing folds of the labia majora 24 with the adhesive layer 14 contacting the clitoris 28 by covering the clitoral shaft 30. The adhesive layer 14 is protected from body fluids and, in its position, physically stimulates the clitoris 28 to provide a strong inhibitory effect on the bladder, relieving stress urinary incontinence.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the following claims.

The invention claimed is:

1. A method for treating female urinary incontinence, comprising applying an adhesive directly to a clitoris of a person suffering from female urinary incontinence.

2. The method of claim 1 in which the adhesive is on one side of a backing sheet formed of a flexible, impervious film material.

3. The method of claim 1 in which, prior to application of the adhesive, the adhesive is protected by a release sheet.

4. The method of claim 1, wherein the applying is performed in a non-clinical environment.

5. The method of claim 1, wherein electrical stimulation or electric devices are not involved.

6. The method of claim 1 wherein the adhesive is applied to the clitoral hood.

7. A method for treating female urinary, incontinence, comprising applying a patch directly to a clitoris of a person suffering from female urinary incontinence, the patch being formed of a backing sheet of flexible, film material with adhesive on one side of the backing sheet, the adhesive being applied directly to the clitoris.

8. The method of claim 7 wherein the adhesive is applied to the clitoral hood.

9. The method of claim 7 wherein the film material is impervious.

\* \* \* \* \*

UNITED STATES PATENT AND TRADEMARK OFFICE
CERTIFICATE OF CORRECTION

PATENT NO. : 8,684,008 B2
APPLICATION NO. : 12/999114
DATED : April 1, 2014
INVENTOR(S) : Cora St. Anne It is certified that error appears in the above-identified patent and that said Letters Patent is hereby corrected as shown below:

IN THE CLAIMS:

In column 5 at line 7, In Claim 7, change "urinary," to --urinary--.

Signed and Sealed this
Twenty-eighth Day of April, 2015

Michelle K. Lee
*Director of the United States Patent and Trademark Office*